United States Patent [19]
Falconer

[11] Patent Number: 6,021,928
[45] Date of Patent: Feb. 8, 2000

[54] TAP FOR DRAINAGE BAG, AND A METHOD OF ASSEMBLY

[75] Inventor: Malcolm I. Falconer, London, United Kingdom

[73] Assignee: Bristol-Myers Squibb Company, New York, N.Y.

[21] Appl. No.: 09/067,422

[22] Filed: Apr. 28, 1998

[30] Foreign Application Priority Data

May 21, 1997 [GB] United Kingdom .................. 9710472

[51] Int. Cl.⁷ ...................................................... B67D 3/00
[52] U.S. Cl. ........................................... 222/554; 251/310
[58] Field of Search .................................... 222/553, 554; 251/310

[56] References Cited

U.S. PATENT DOCUMENTS 4,462,510  7/1984  Steer et al. ............................. 222/554
4,632,362  12/1986  Lucking ................................. 222/553

FOREIGN PATENT DOCUMENTS 2520471  7/1983  France ................................. 251/310
90/05696  5/1990  WIPO ................................... 222/553

Primary Examiner—Philippe Derakshani
Attorney, Agent, or Firm—Stuart E. Krieger

[57] ABSTRACT

A tap (14) for a drainage bag (10) is provided which can be welded to the bag material with the tap in a ready-assembled condition. The tap includes an integral attachment portion (20) and a housing (18). An L-shaped tubular tap member (16) with a handle (30) is inserted in an aperture of the housing (18), and is rotatable in the aperture between a closed position in which the outlet (22) points upwardly, and an open position in which the outlet (22) points downwardly. In the closed position, a peripheral region (54) of the attachment portion (20) projects beyond the tap member (16) on all sides, to enable the assembled tap to be welded to the bag material.

7 Claims, 4 Drawing Sheets

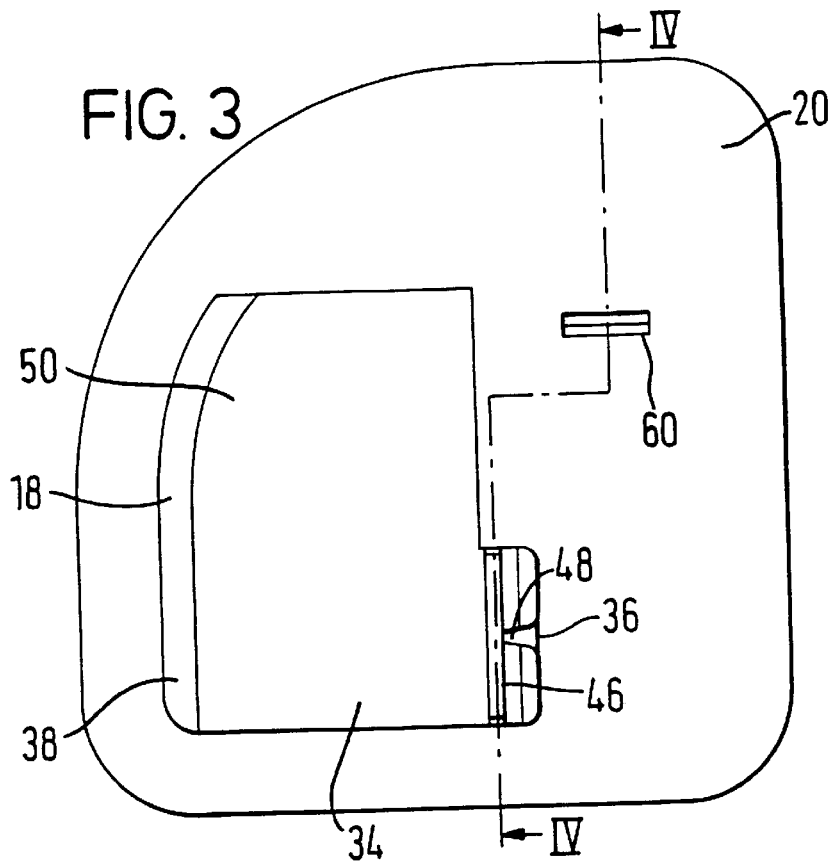
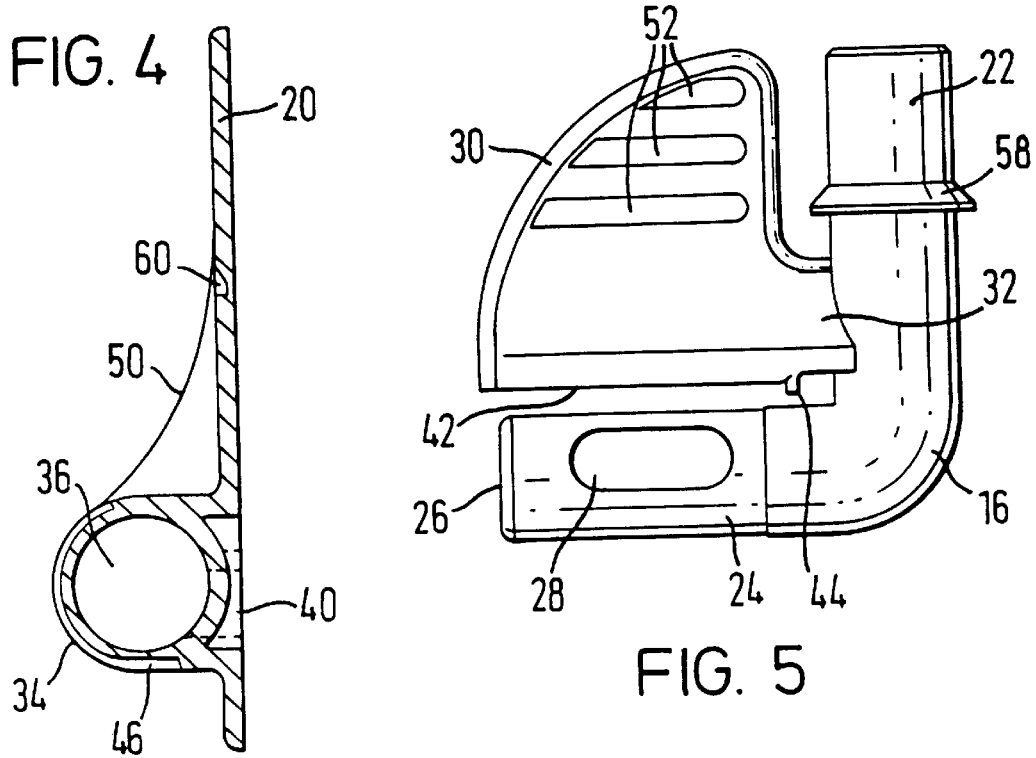

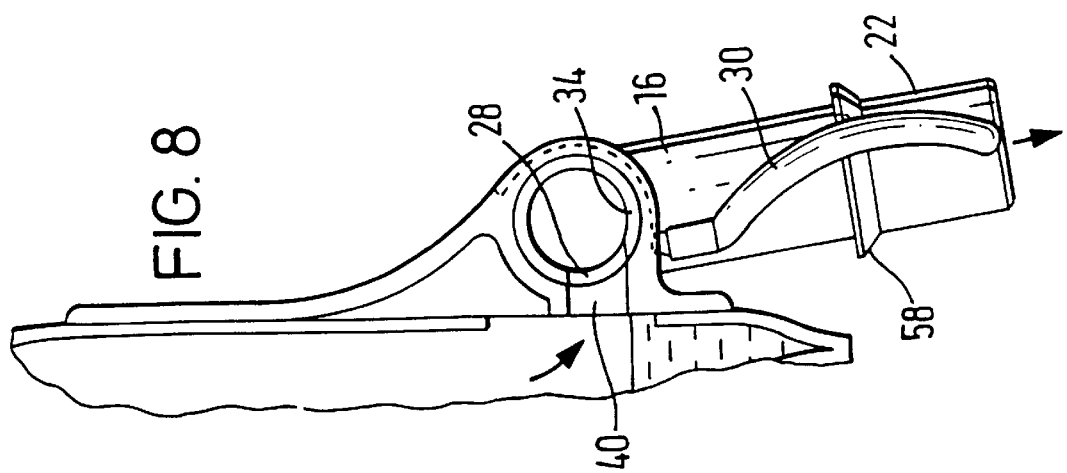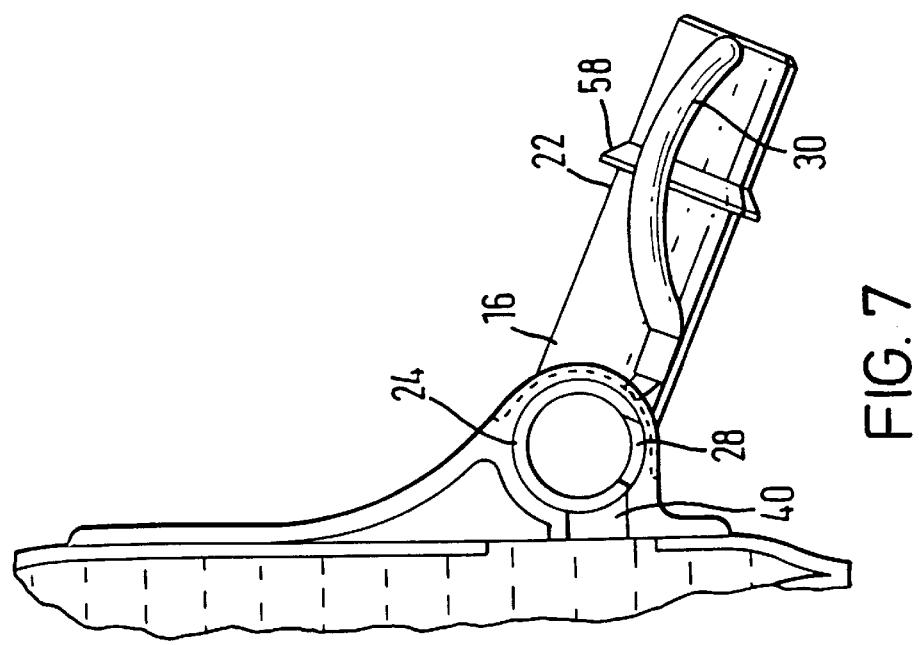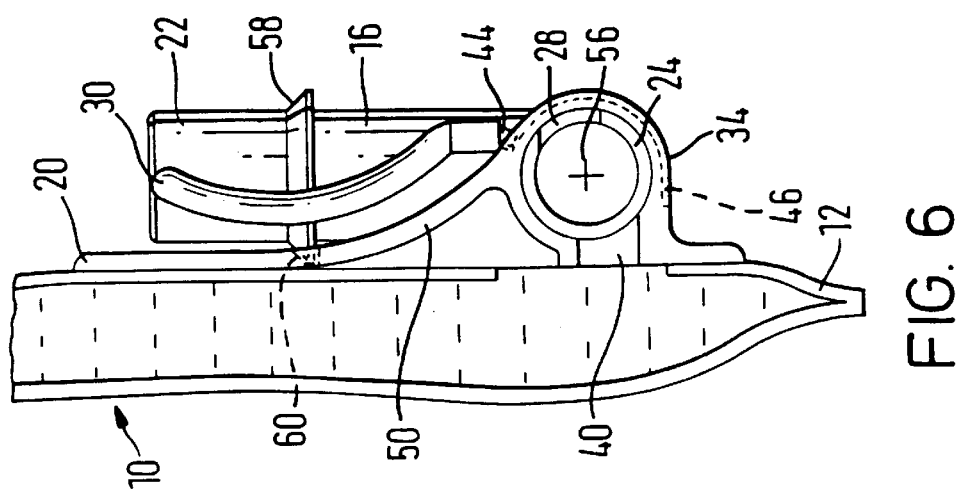

TAP FOR DRAINAGE BAG, AND A METHOD OF ASSEMBLY

BACKGROUND OF THE INVENTION

This invention relates to a tap for a drainage bag, for example, for body waste or body fluids, and to a method of bag assembly.

Many designs of tap for drainage bags are known. Typically, the tap consists of a rotatable tap member received within an aperture of a tap housing. The housing has a base portion to enable it to be sealed face-to-face to a wall of the drainage bag. For example, such tap constructions are illustrated in GB-A-2101274, GB-A-2288865 and GB-A-2163235, WO 95/29651 and WO 93/17642.

Generally, with such constructions, the base is first welded to the exterior wall of the pouch, after which the tap member is inserted into the aperture to complete the assembly.

SUMMARY OF THE INVENTION

In one aspect, the present invention provides a tap for a drainage bag, the tap comprising a housing, and a tap member having a portion rotatable within the aperture of the housing, the housing having an attachment portion which can be welded to a drainage bag with the tap member assembled to the housing.

Preferably, the tap is weldable to the drainage bag in an operative condition. In one form, the tap is weldable at least in a normally closed condition.

It has been appreciated, in the course of the work resulting in the invention, that significant advantages (e.g. simplified assembly and more efficient manufacture) can be achieved by being able to assemble a tap prior to welding to a bag, and to weld the tap in a ready assembled condition.

Firstly, it is possible to test the tap prior to fitting to the bag, in exactly the same condition as it will be fitted to the bag. With prior art designs of tap, it is only possible to test the tap in such a condition after the tap has been assembled following attachment of a part of the tap to the wall of the bag. This makes the tap considerably more difficult to handle and to test. Of course, it would be possible with prior art taps to assemble the tap, subject the tap to a test, and then disassemble the tap again prior to welding to the bag wall. However, in general the taps are not designed to be disassembled, and the disassembly process may damage the tap parts.

Secondly, the ability to be able to weld a ready-assembled tap to the material for the bag wall can simplify considerably the manufacturing process. In particular, it is much easier to manipulate and assemble the tap components prior to welding to the bag material. Furthermore, by assembling the tap before welding, the number of separate parts which have to be handled later in the manufacturing process can be reduced.

Preferably, the region of the tap intended to be attached to the bag wall material extends peripherally beyond the tap member, at least when the tap member is in a predetermined operating position (for example, the open position, or the closed position, or a part-way open position). This is advantageous because it enables a welding tool to apply pressure directly to the peripherally extending or projecting region at positions all around the tap. The application of direct pressure can be important in enabling a strong and reliable weld seal to be produced. If a particular region is not subjected to direct pressure, the weld in that region may be faulty or weak.

Preferably, the tap member is rotatable about an axis which is generally perpendicular to the direction of liquid flow from the tap outlet when the tap is in an open position.

Preferably, the tap comprises an outlet tube which is movable between a deployed position in which the outlet tube projects downwardly from the tap (when the tap is open), and a stowed position in which the outlet tube does not project downwardly from the tap. Preferably, in the stowed position, the tap points generally away from the direction of the outlet tube when in the open position.

Other types of tap different from the examples discussed above are also known, for example, as illustrated in GB-A-2150031. However, such a tap does not have a rotatable tap member, and is not of an assemblable type. Furthermore, it would not be possible to weld the tap to the bag material with the tap in an operative condition.

In a related aspect, the invention provides a tap for a drainage bag, the tap comprising a tap member having a portion rotatable within an aperture of a housing, and an attachment portion, wherein, when the tap member is in at least a predetermined position, a peripheral region of the attachment portion projects beyond the tap member around substantially the entire periphery of the attachment portion.

In a further related aspect, the invention provides a method of producing a drainage bag, the method comprising welding to sheet material forming, or for forming, a wall of the bag, a tap in a ready-assembled condition.

In a further related aspect, the invention provides a tap having a tap member rotatable within an aperture of a housing, and an attachment portion which can be welded to a drainage bag with the tap member assembled to the housing.

BRIEF DESCRIPTION OF THE DRAWINGS

An embodiment of the invention is now described by way of example only, with reference to the accompanying drawings, in which:

FIG. 3 is a front view of the tap housing;

FIG. 4 is a cross-section along the line IV—IV in FIG. 3;

FIG. 5 is a front view of the tap member;

FIG. 6 is a schematic side view of the tap when in the position shown in FIG. 1;

FIG. 7 is a schematic side view similar to FIG. 6, but showing the tap member just prior to opening;

FIG. 8 is a schematic side view of the tap in the position shown in FIG. 2; and

DETAILED DESCRIPTION OF THE DRAWINGS

Figure 2:
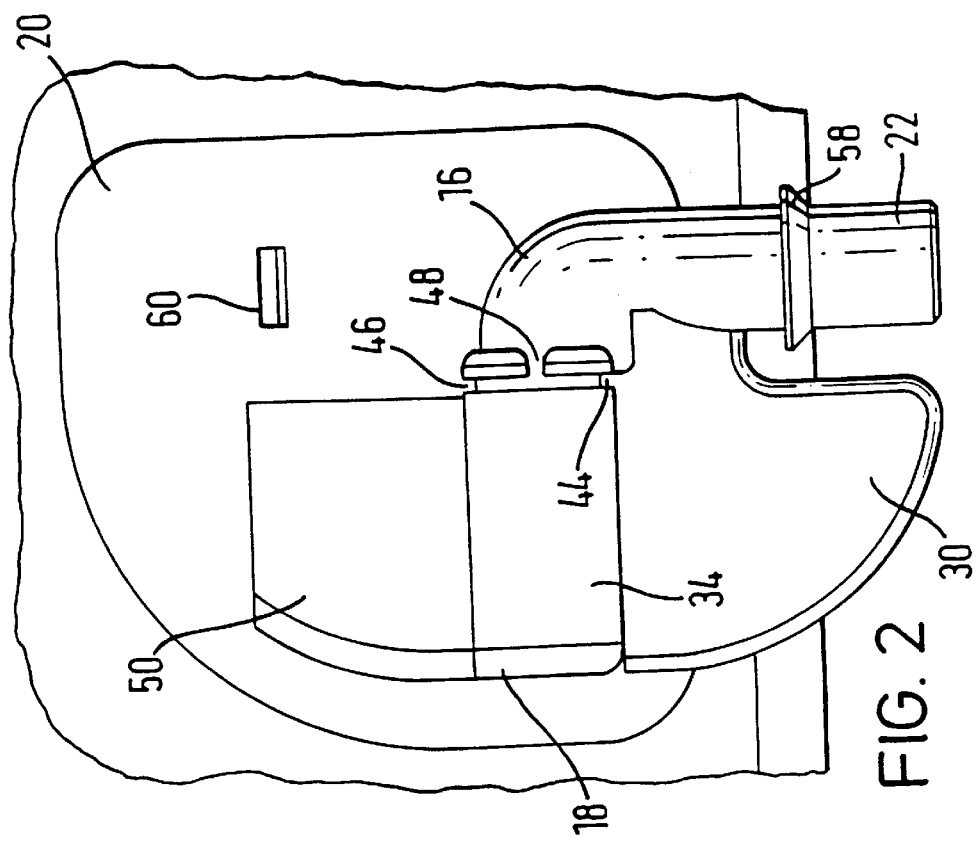
FIG. 2 is a front view similar to FIG. 1, but showing the tap in its deployed (open) position.

Referring to the drawings, a urine bag 10 has on its front wall 12 (i.e. the wall facing away from the skin of the wearer) a tap 14 for venting urine, positioned adjacent to the lower peripheral seam of the bag 10. The tap 14 is of a two-part design, and consists of a tap member 16 rotatably mounted within a tap body 18 which has an integral (usually substantially flat) attachment portion 20 welded to the wall 12 of the drainage bag.

Referring to FIG. 5, the tap member 16 includes a generally L-shaped tube, one limb of which forms an outlet tube 22, and the other limb of which forms a barrel 24 rotatably mounted to the body 18. The barrel 24 has an elongate aperture 28 through its circumferential wall through which fluid passes when the tap is in an open condition (as described further below). The tap member 16 further has an integral handle 30 joined to the outlet tube 22 by a web 32. In use, the handle 30 allows the tap member 16 to be rotatably moved between a closed position (as seen in FIGS. 1 and 6) in which the outlet tube 22 and the handle 30 point generally upwardly, and an open position (as seen in FIGS. 2 and 8) in which the outlet tube 22 and the handle 30 point generally downwardly.

Referring to FIGS. 3 and 4, the body 18 consists of a tubular housing 34 carried on the front face of the attachment portion 20. The tubular housing is dimensioned to receive the barrel 24 of the tap member 16, and has an open end 36 into which the barrel 24 is inserted during assembly of the tap, and a closed end 38. As best seen in FIG. 4 (and also seen schematically in FIGS. 6–8), the tubular housing 34 includes an aperture 40 in the circumferential wall facing the bag wall 12, to allow fluid in the bag to communicate with the tap member 16.

Figure 1:
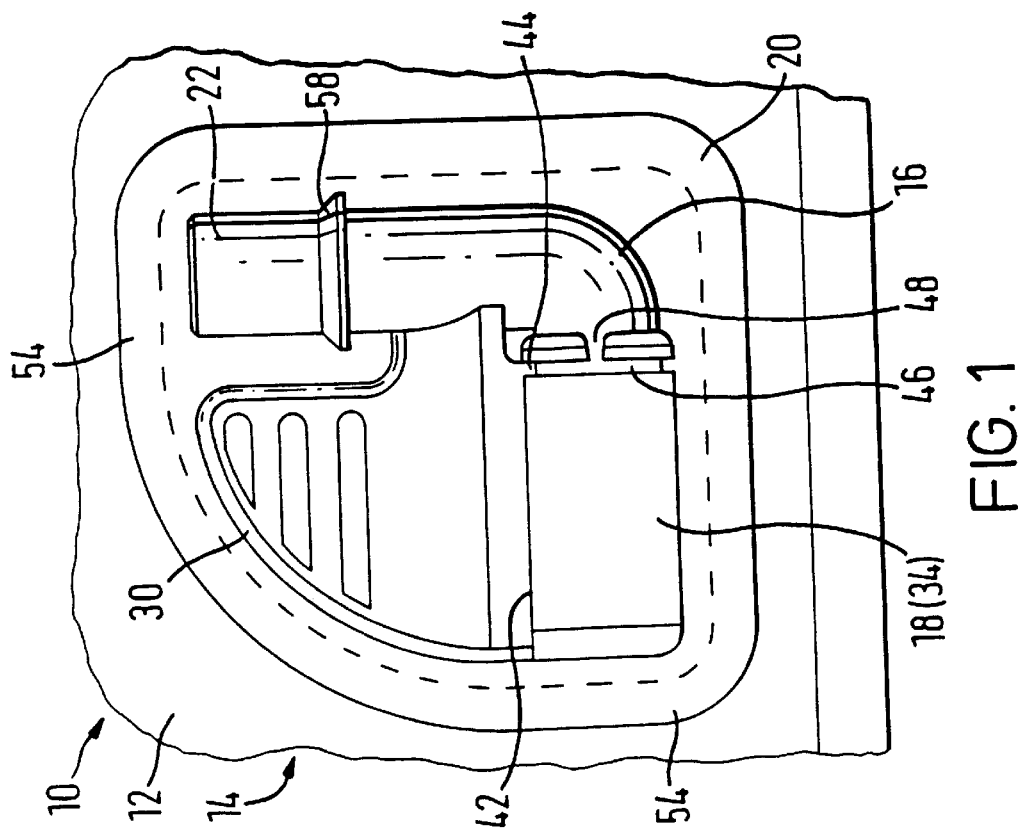
FIG. 1 is a front view of a tap attached to a urinary bag, the tap being shown in the stowed (closed) position.

As can be seen in FIGS. 1 and 2, the handle 30 has a rear edge 42 which, when the tap is assembled, lies adjacent to the outer circumferential surface of the tubular housing 34. At the end of the edge 42 adjacent to the web 32, the handle 30 is formed with a small projection 44 which is received in an annular recess 46 adjacent to the open end 36 of the tubular housing 34. In use, the projection 44 slides in the recess 46 as the tap member 16 is moved between the open and closed positions, and serves to hold the tap member 16 captive within the tubular housing 34. A small, tapered entry notch 48 is provided to enable the projection 44 to be fitted into the recess 46 when the barrel 24 is inserted into the tubular housing 34. The notch 48 is arranged such that the tap member 16 has to be orientated generally perpendicularly to the attachment portion 20 to enable the projection 44 to pass through the notch 48. The notch is slightly undersized, and has tapered sides, such that the projection 44 can be forced through the notch 48 with a "snap-action", and is difficult to remove thereafter. It will be appreciated that by positioning the notch 48 in this manner, the tap member can only be fitted to (and possibly forcibly removed from) the housing 18 when it is midway between the open and closed positions. Thus, when the tap is in either the open or closed position, the projection 44 will not be in register with the notch 48, and there will be virtually no danger of the tap member 16 being removed accidentally from the housing 18, even if a strong force is accidentally applied.

As best seen in FIGS. 6–8, the handle 30 has a curved profile, and (referring also to FIGS. 3 and 4) the body 18 includes a curved ramp region 50 to match the profile of the handle 30. When the tap is in its fully closed position, the handle 34 lies adjacent to the curved ramp 50. This reduces the risk of the tap accidentally being pulled open by an object becoming caught behind the handle 30. As can be seen in FIGS. 1 and 5, the front face of the handle is formed with a plurality of small recesses 52 to provide a finger grip surface.

An important feature of this embodiment is that the attachment portion 20 is dimensioned to be larger than the tap member 16, such that a peripheral region (54 in FIG. 1) projects beyond the tap member 16 on all sides (when the tap member is in its fully closed position). This feature enables the tap 14 to be welded to the wall 12 of the bag 10 in a fully-assembled condition. The clearance between the tap member 6 and the outer peripheral edge of the attachment portion 20 enables a welding head (such as an RF welding head, or an induction welding head) to be brought closely adjacent to the peripheral region 54, to form a closed welded seam between the peripheral region 54 and the underlying bag wall material. To the best of the inventor's knowledge and belief, such a technique of welding a ready-assembled tap to the bag wall material has not been used hitherto. The prior art designs (e.g. those discussed previously) do not employ a projecting peripheral region 54 which would enable a ready-assembled tap to be welded to the bag wall material. Before welding, the tap member 16 can be assembled to the body 18 by inserting the barrel 24 into the open end 36 of the tubular housing 34, as described above. The tap member can be assembled on site, or supplied as a ready-assembled unit. If desired, the assembled tap 14 can be tested (or selected random samples from a batch of taps can be tested) prior to fitting to the bag wall material.

The operation of the tap is illustrated in FIGS. 6–8. Referring to FIG. 6, in the fully closed position of the tap member 16, the slot 28 in the barrel 24 is completely out of alignment with the aperture 40 in the tubular housing 34, and so there is no liquid flow through the tap. To "open" the tap 14, the tap member 16 is rotated clockwise (as shown in the drawing) about an axis 56. As the tap member reaches its fully open position (FIG. 8) the slot 28 in the barrel 24 comes into alignment with the aperture 40 in the tubular housing 34. Liquid flows through the apertures 40 and 28 into the barrel 24 of the tap member 16, and away through the outlet tube 22. It will be appreciated that the angle at which the tap opens to fluid flow can be determined by the relative positions of the apertures 28 and 40. In the present embodiment, the aperture 28 is not positioned symmetrically about the axis 56, but is "retarded". The apertures 28 and 40 only come into alignment once the tap member 16 has been rotated well below the horizontal position (see FIG. 7) which can ensure that the bag contents do not spurt out unexpectedly before the tap member is pointing downwardly. It will also be appreciated that the use of elongate slot-shaped apertures can provide a large cross-sectional area, with a relatively small amount of angular movement being required to move the tap between its fully open position (FIG. 8) and a position (FIG. 7) in which the liquid flow is cut off.

The outlet tube is formed with an annular ridge 58. This enables an external drainage tube (not shown) to be coupled to the outlet tube 22 with a snap-fit connector (e.g. as described in EP-A-0 753 323). For example, the tap may be left open at night, and coupled to an external drainage tube, for example, while the wearer is asleep. A recess 60 is provided in the attachment portion 20 of the body 18 to accommodate a portion of the bead 58 when the tap member 16 is in its fully closed position. The recess 60 allows the tap member to lie almost flat against the attachment portion 20.

Figure 9:
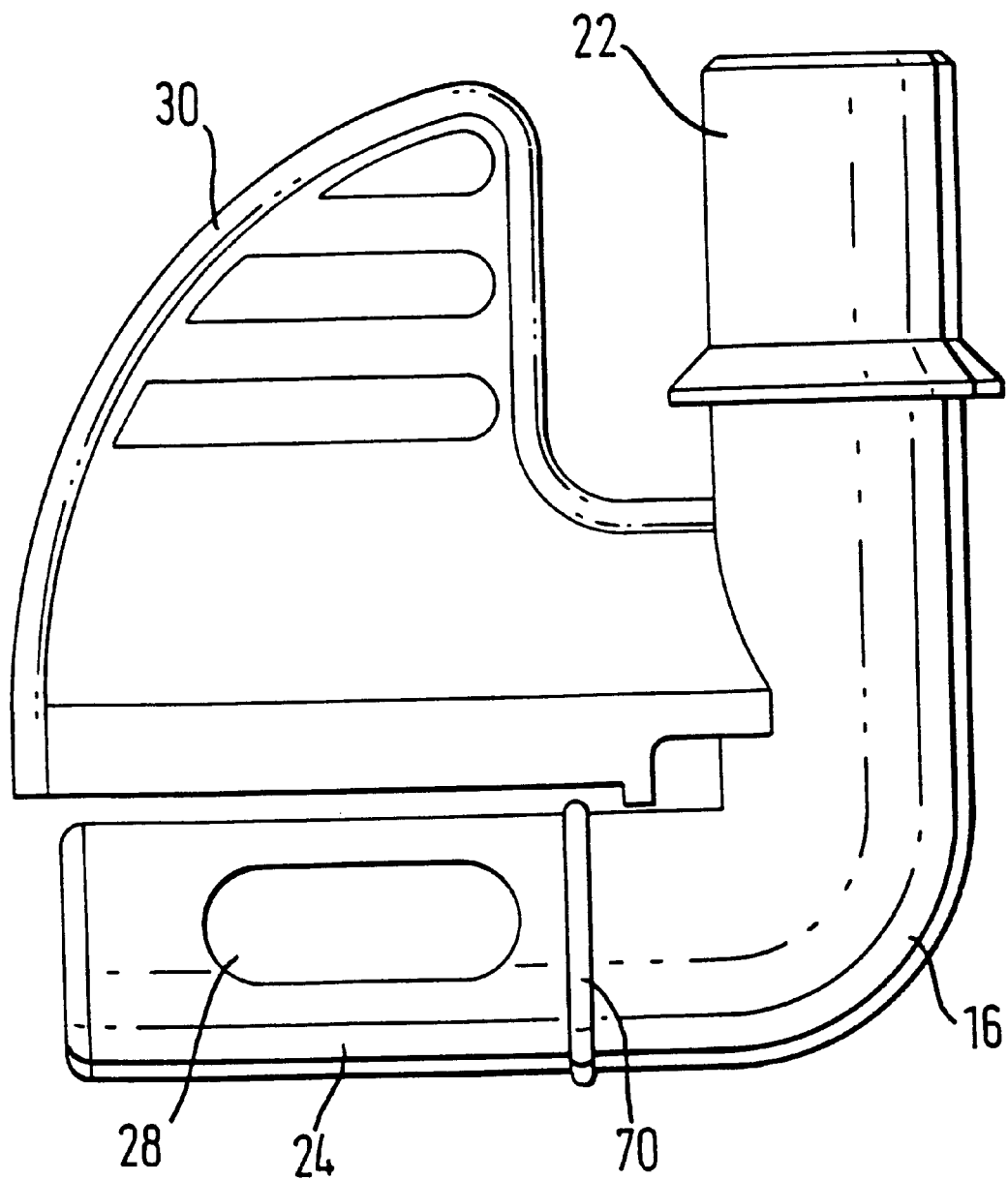
FIG. 9 is a front view of a modified design of tap member.

FIG. 9 illustrates a modified design of tap member 16 which includes an annular sealing ridge 70 positioned on the barrel 24 so that it will be near the mouth of the tubular housing 34. The ridge 70 may be of elastomeric material, and provides a seal between the barrel 24 and the interior surface of the tubular housing 34. As an example, the ridge 70 could be formed by an O-ring which is fitted over the barrel 24 and retained in position by, for example, seating in an annular recess. As an alternative example, the ridge 70 could be moulded integrally on the barrel 24 using a multi-shot (for example, 2-shot) moulding process (known per se). Other forms of seal, such as a narrow blade, or a frusto-conical wiper, may also be used and may, for example, be moulded of the same material as the barrel 24 if desired.

Although the invention has been described above in relation to a urine drainage bag, it will be appreciated that the invention may be used with any form of drainage bag (particularly, but not exclusively, drainage bags for body fluids or body waste) to enable the bag contents to be drained away.

It will be appreciated that the invention enables a tap to be assembled and welded to the bag wall material in a ready-assembled condition. Not only does this enable the tap to be tested prior to being welded, it also can simplify the manufacturing process by enabling the tap parts to be manipulated more easily during assembly of the tap, and by reducing the number of individual parts which have to be handled during fitting to the bag.

The particular embodiment described above is also advantageous for the following reasons:

(a) In the fully-open position, the outlet tube 22 projects downwardly below the edge of the bag, which can prevent any of the liquid content from running onto the bag surface when the tap is open.

(b) In the fully-closed position, the tap member is "stowed" so that it does not project below the bag. This can increase the comfort for the wearer, and reduce the possibility that the outlet tube 22 may catch on the wearer's clothing. Furthermore, since the outlet tube points upwardly when in the fully-closed position, there will be no tendency for any liquid remaining in the outlet 22 to drip out, as may happen with a permanently downwardly-pointing tube.

(c) The large handle 30 enables a user easily to manipulate the tap. Furthermore, the handle "points" in the same direction as the outlet tube 22, so that the user can readily identify whether the tap is open or closed.

(d) The tap member 16 can be easily assembled to the body 18 by aligning the tap member in the "midway" position, and inserting the barrel 24 into the open end 36 of the tubular body 34. The notch 48 permits the projection 44 of the handle 30 to pass easily into the recess 46. Thereafter, the tap member 16 is held captive in the housing.

It will be appreciated that the foregoing description is merely illustrative of a preferred embodiment of the invention, and that many modifications may be made within the scope of the present invention.

I claim:

1. A tap for a drainage bag, comprising a housing having an aperture, a tap member having a portion insertable and rotatable within said aperture of said housing between an open and closed condition, said housing having an attachment portion weldable to the drainage bag when said tap member is within said housing, said housing having a fluid inlet and outlet, said tap member being rotatable about an axis which is substantially perpendicular to the direction of flow of liquid from said outlet of said housing when said tap member is in an open condition, said tap being movable between a projecting position when said tap is in an open condition, and a non-projecting position when said tap member is in a closed condition and, retaining means for retaining said tap member captive relative to said housing, said retaining means including a projection on one of said tap member and housing, and a recess on the other of said tap member and housing in which said projection is received.

2. The tap according to claim 1, wherein said outlet is integral with the said tap member.

3. The tap according to claim 1, wherein said tap member comprises an angled tube.

4. The tap according to claim 1, wherein said tap member has an elongated slot in one arm through which liquid can pass to said outlet when said slot is aligned or substantially aligned with a corresponding aperture in the housing.

5. The tap according to claim 1, wherein said tap member has an integral handle.

6. The tap according to claim 1, wherein said outlet points in a first direction when said tap member is in a fully open condition, and in a second generally opposite direction.

7. A method of assembling a drainage bag with a tap, the steps comprising:

forming a drainage bag from plastic film, said bag having an internal and external surface, assembling said tap from separate tap components, said components including a housing having an aperture, a tap member having a portion insertable and rotatable within said aperture of said housing between an open and closed condition, said housing having an attachment portion weldable to the drainage bag when said tap member is within said housing, said housing having a fluid inlet and outlet, said tap member being rotatable about an axis which is substantially perpendicular to the direction of flow of liquid from said outlet of said housing when said tap member is in an open condition, said tap being movable between a projecting position when said tap is in an open condition, and a non-projecting position when said tap member is in a closed condition and, retaining means for retaining said tap member captive relative to said housing, said retaining means including a projection on one of said tap member and housing, and a recess on the other of said tap member and housing in which said projection is received;

testing said tap for leakage; and welding said attachment portion of said tap to an external surface of the drainage bag.

* * * * *